United States Patent
Sung et al.

(10) Patent No.: US 7,263,166 B2
(45) Date of Patent: Aug. 28, 2007

(54) REMOTE CONTROL HANDSWITCH AND OPERATING METHOD THEREOF FOR PORTABLE X-RAY UNITS

(75) Inventors: Ki-Bong Sung, Goyang (KR); Hack-Seoug Kim, Goyang (KR)

(73) Assignee: Postkom Co., Ltd, Goyang (KR)

( * ) Notice: Subject to any disclaimer, the term of this patent is extended or adjusted under 35 U.S.C. 154(b) by 162 days.

(21) Appl. No.: 10/751,472

(22) Filed: Jan. 6, 2004

(65) Prior Publication Data
US 2005/0047547 A1 Mar. 3, 2005

(30) Foreign Application Priority Data
Aug. 29, 2003 (KR) ............ 10-2003-0060045

(51) Int. Cl.
*H05G 1/56* (2006.01)
(52) U.S. Cl. .................................... 378/114
(58) Field of Classification Search .......... 378/114; 200/341, 523, 524
See application file for complete search history.

(56) References Cited

U.S. PATENT DOCUMENTS

| 4,170,735 | A | * | 10/1979 | Codina et al. ............ 378/96 |
| 5,206,894 | A | * | 4/1993 | Makrinos et al. ......... 378/93 |
| 5,555,120 | A | * | 9/1996 | Telymonde et al. ....... 378/93 |
| 6,285,742 | B1 | * | 9/2001 | Haumann et al. ........ 378/116 |
| 6,704,506 | B2 | * | 3/2004 | Sasagawa ................. 396/88 |
| 6,801,594 | B1 | * | 10/2004 | Ali et al. ................ 378/4 |

* cited by examiner

*Primary Examiner*—Jurie Yun
(74) *Attorney, Agent, or Firm*—Laurence A. Greenberg; Werner H. Stemer; Ralph E. Locher (57) ABSTRACT

The present invention relates to a remote control handswitch for a portable X-ray unit. The remote control handswitch for a portable X-ray unit comprises a two-step switch formed of a standby button and an execution button, and a handswitch housing having the two-step switch on an upper side of the same, wherein a multi-function operation is performed based on a click operation of the two-step switch. In the present invention, the remote control handswitch may be used for a remote controller using a remote control handswitch.

12 Claims, 8 Drawing Sheets

REMOTE CONTROL HANDSWITCH AND OPERATING METHOD THEREOF FOR PORTABLE X-RAY UNITS

BACKGROUND OF THE INVENTION

1. Field of the Invention

The present invention relates to a remote control handswitch for a portable X-ray unit, and in particular to a remote control handswitch for a portable X-ray unit capable of achieving a multifunction operation based on a click operation of a two-step switch.

2. Description of the Background Art

A conventional portable X-ray unit is classified into a fixed type and a mobile type based on a state that it is portable or not. The portable X-ray unit represents a portably movable X-ray unit that does not have any limit for the place of use.

In addition, a controller capable of controlling a conventional X-ray photographing apparatus is adapted to properly adjust a tube voltage by an input voltage adjusting unit, and a direct or indirect photographing operation is selective. An exposure degree of an X-ray is properly set. There is provided a numbering display unit. An operator controls all functions of a photographing apparatus using a controller through a microphone connected with a speaker in the side of a camera obscura.

SUMMARY OF THE INVENTION

Accordingly, it is an object of the present invention to provide a remote control handswitch for a portable X-ray unit capable of achieving a multifunction operation based on a click operation of a two-step switch of a remote control handswitch.

To achieve the above objects, there is provided a remote control handswitch for a portable X-ray unit comprising a two-step switch formed of a standby button and an execution button, and a handswitch housing having the two-step switch on an upper side of the same, wherein a multifunction operation is performed based on a click operation of the two-step switch.

BRIEF DESCRIPTION OF THE DRAWINGS

The present invention will become better understood with reference to the accompanying drawings which are given only by way of illustration and thus are not limitative of the present invention, wherein.

DETAILED DESCRIPTION OF THE PREFERRED EMBODIMENTS

A remote control handswitch for a portable X-ray unit according to the present invention can achieve a multifunction operation based on a pressing time and number of a standby button and an execution button of a press button unit.

In a portable X-ray unit, a remote control switch function using a handswitch is capable of controlling a kV, mAs setting and a memory selection or a collimator lamp on and off operation and a laser pointer lighting operation. Only a standby button is used for performing a remote control using a handswitch.

In order to use a remote control mode, a standby button of a handswitch is pressed by a series triple click operation, for example, wherein each click lasts a short time, i.e., about one second. After a completion of the operation, the mode is switched to a remote control mode of the handswitch. When the remote control mode is performed, the LEDs displaying the memory number of the preset memory are sequentially turned on and off. The LEDs displaying the kV and mAs values stored in each memory are sequentially blinked and continuously scrolled. In the above continuous scroll, in order to select a desired memory, the kV and mAs values stored in the memory number are displayed by pressing the standby button one time at the time when the LED of the memory number is turned on.

The just earlier data is stored and displayed as the values of all preset memory.

After the memory selection, the changing method of the kV value is performed based on a continuous triple click operation using the standby button of the handswitch like a method for performing a remote control mode. After the standby switch is continuously triple clicked, when the kV display LED is blinked after the memory storing number LED, the kV selection mode is displayed by pressing the standby button of the handswitch one time. In the kV selection mode, the kV value is increased by pressing the standby button of the handswitch one time. In addition, the LED of the kV value is fast blinked by continuously pressing the standby button of the handswitch, representing that the kV value is fast increased or is fast decreased. In a state that the standby button is continuously pressed, when the kV value is displayed, and the standby button of the handswitch is pressed, it is possible to select a corresponding kV value. After the kV value is selected, the kV values are automatically set up for a few seconds.

After the kV value is set up, the changing method of the mAs value is similar with the change of the kV value. The standby button of the handswitch is triple clicked like the method for performing the remote control mode. After the standby button is clicked three times, the kV display LED is blinked after the memory LED, and the mAs LED is blinked. When the standby button of the handswitch is clicked one time, the current mode is switched to the mAs selection mode. In the kV selection mode, the mAs selection mode is automatically performed after the kV value is set up. In the mAs selection mode, the standby button of the handswitch is clicked one time, so that the mAs value is increased by one step. When the standby button of the handswitch is continu ously pressed, the LED displaying the mAs value is fast blinked for displaying the fast increase of the values or the fast decrease of the values. In a state that the standby button is continuously pressed, when stopping the pressing state of the standby button of the handswitch, it is possible to select a desired mAs value at the stop point. After the mAs velue is selected, the mAs value is automatically set up after a few seconds.

In order to turn on or off the lighting of the laser pointer using the remote control handswitch of the portable X-ray unit, the standby button of the two-step switch is pressed two times, the lighting of the laser pointer is turned on. After the lighting of the laser pointer is turned on, the lighting of the laser pointer is automatically turned off after 30 seconds.

In addition, after the X-ray unit is performed, the lighting of the laser is automatically turned off.

In order to turn on the collimator using the remote control handswitch of the portable X-ray unit, the standby button of the two-step switch is pressed two times, so that the collimator is turned on. The collimator us automatically turned off in 30 seconds after the collimator is turned on.

In the portable X-ray unit, the turning on and off operations of the laser pointer, the lighting and the collimator may be concurrently performed by the same operation method.

When the collimator is turned on, the filament is heated by pressing the same for a second. When the collimator is turned off, the filament is heated in 0.8 seconds by pressing the standby button for a second. After the filament is heated, the mode becomes a standby state, and the X-ray unit gets standby.

In the two-step switch unit, the pressing operation for a second represents a button press for a short time period, and the pressing operator for a long time period represents a state that the button is pressed until the mode is selected to the selection mode. In the pressing operation for a second, the idle time is within 0.8 seconds when continuously pressing the button two times or three times.

The preferred embodiments of the present invention will be described with reference to the accompanying drawings.

Figure 1:
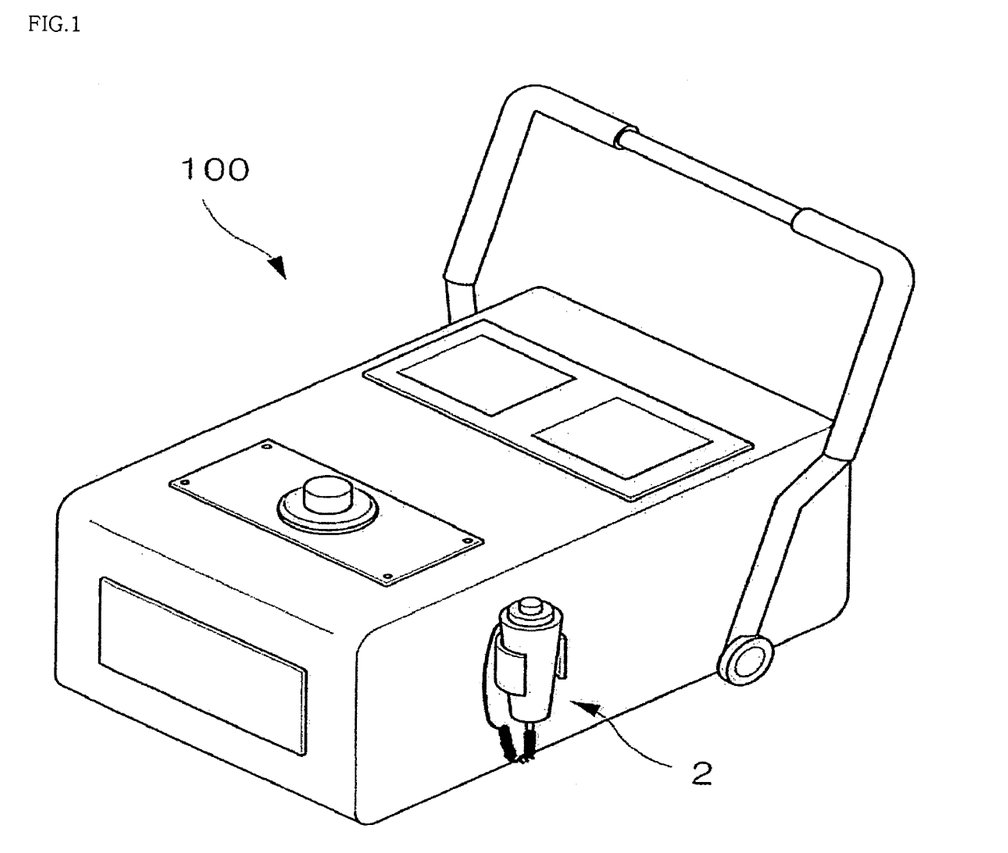
FIG. 1 is a view illustrating a remote control handswitch for a portable X-ray unit according to the present invention.
Figure 2:
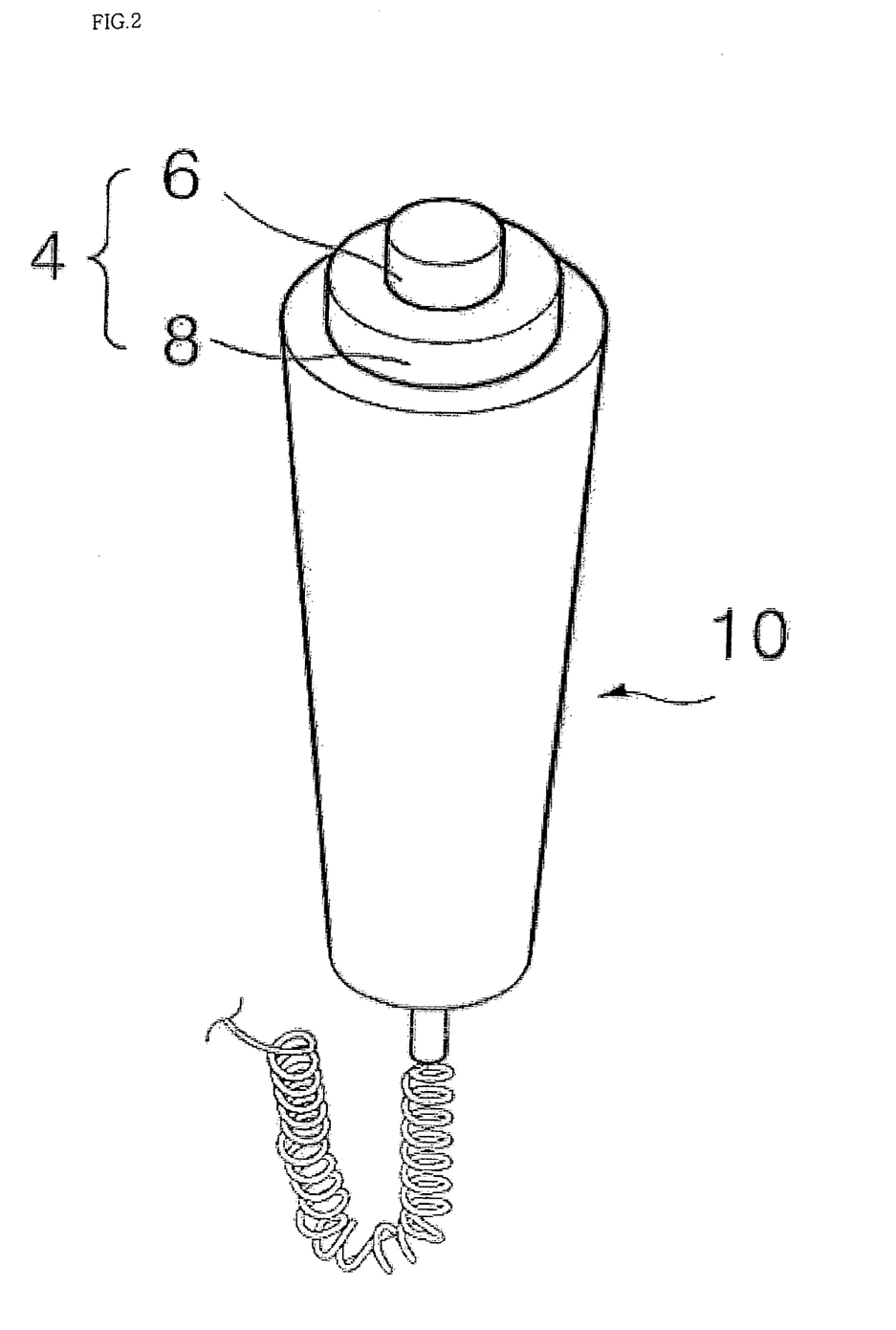
FIG. 2 is a perspective view illustrating a remote control handswitch according to the present invention.

FIG. 1 is a view illustrating the construction of the portable X-ray unit 100 according to the present invention, and FIG. 2 is a perspective view of the remote control handswitch 2 of the portable X-ray unit 100 of FIG. 1. A two-step switch 4 is installed on an upper side and is formed of a standby button 6 and an execution button 8 for achieving a multifunction operation based on a click operation. Referring now to FIG. 9, it can be seen that logic within the unit 100 of FIG. 1 receives an input from the handswitch 2 and controls the multifunction operations described more completely in connection with the flowcharts of FIGS. 3-8.

Figure 3:
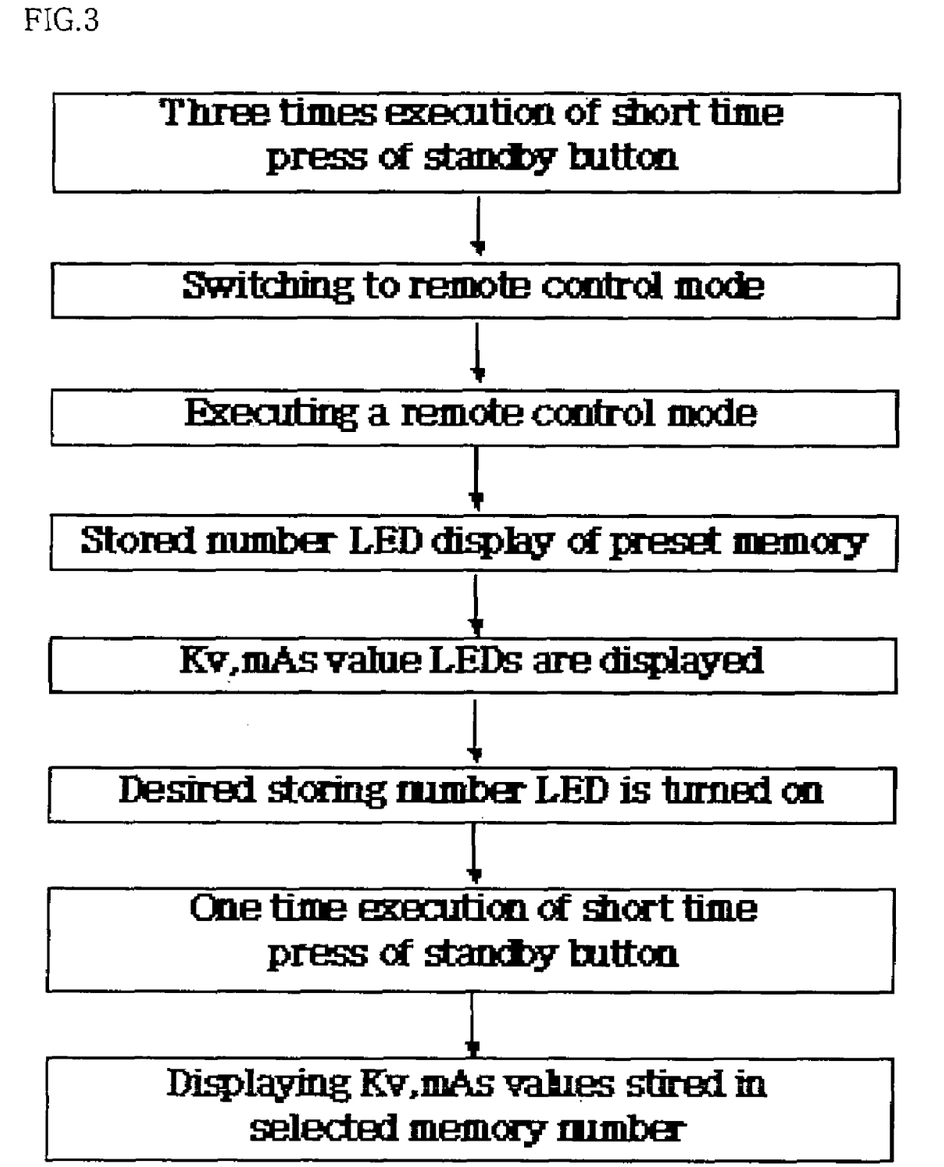
FIG. 3 is a flow chart of a preset memory selection method according to the present invention.

As shown in FIG. 3, in an operation of the remote control handswitch of the portable X-ray unit according to the present invention, the standby button of the two-step switch is triple clicked three times in series, so that the current mode is switched to the remote control mode. After the mode is switched to the remote control mode, the remote control mode is executed. After the remote control mode is executed, the storing number LED of the preset memory are sequentially displayed. The LEDs corresponding to the kV values and mAs value of each memory are sequentially blinked. The storing number LED of the preset memory and the LED displaying the kV value and mAs value stored in the storing number are continuously scrolled. In the above scroll step, at the time when the LED of the storing number is turned on, when the standby button is pressed one time, the kV value and mAs value stored in the memory number are displayed.

Figure 4:
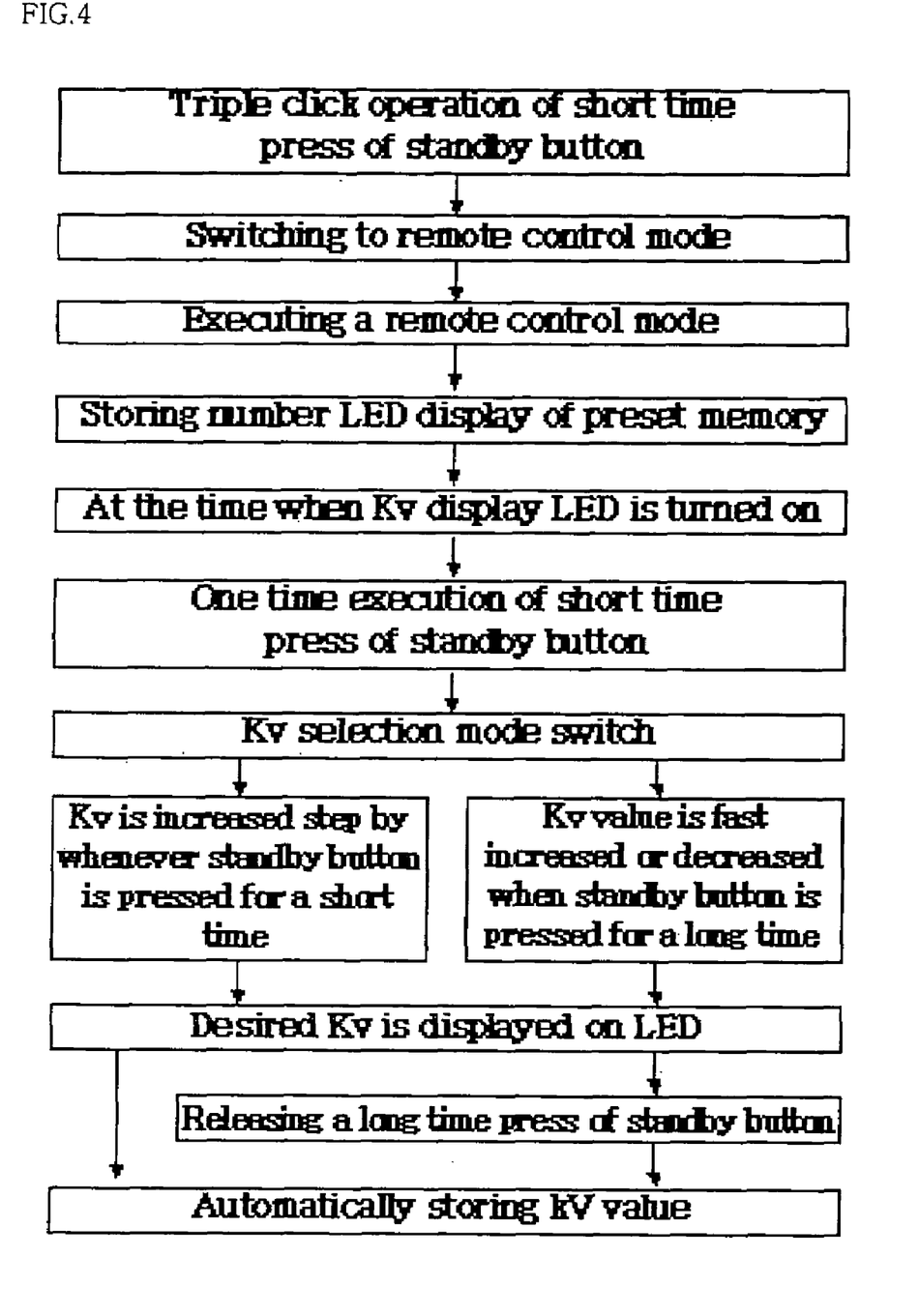
FIG. 4 is a flow chart of a kV-setting change method based on a kV, mAs setting change method according to the present invention.

As shown in FIG. 4, when the standby button of the two-step switch unit is pressed three times (triple clicks), the current mode is switched to the remote control mode. After the mode is changed to the remote control mode, the remote control mode is executed. After the remote control mode is executed, the storing number LEDs of the preset memory are displayed. After the storing number LEDs are sequentially displayed, when the LEDs displaying the kV value and mAs are sequentially blinked, the standby button is pressed for a second one time. After the standby button is pressed one time, the mode is switched to the kV selection mode. The kV value is increased by one step when the standby button is pressed one time. When the standby button is continuously pressed in a pressed state, the LEDs displaying the kV value shows a fast increasing value or a fast decreasing value. In the step in which the kV value is increased by one step, in the case that a desired kV value is displayed on the LED, the kV value is automatically stored in a few seconds. When the standby button is continuously pressed in a pressed state, the LEDs display the fast increasing values and fast decreasing values. In the above procedure, when a desired kV value is displayed on the LED, and the standby button is released at that time, a corresponding kV value is selected. In the step for selecting the kV value, the kV value is automatically stored in a certain time period.

Figure 5:
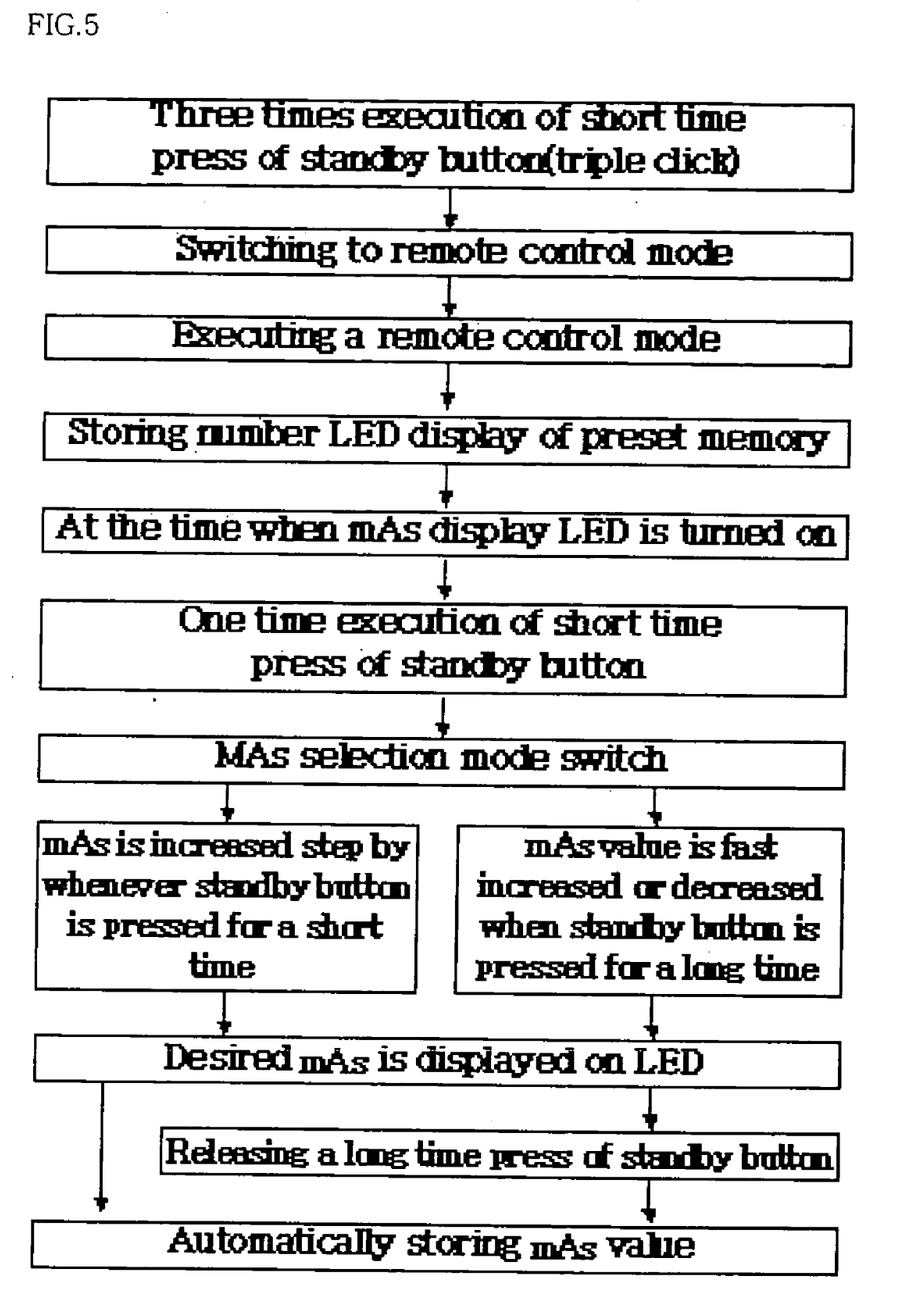
FIG. 5 is a flow chart of a mAs setting change method according to the present invention.

FIG. 5 is a flow chart of a mAs setting change method based on the kV and mAs setting change methods according to the present invention.

Figure 6:
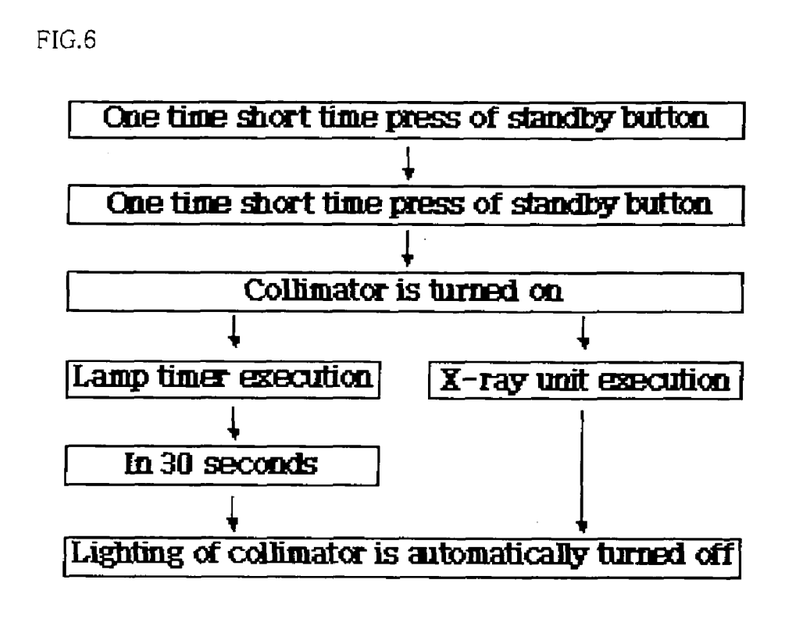
FIG. 6 is a flow chart of a collimator on and off selection method according to the present invention.

FIG. 6 is a flow chart of an on and off selection method of the collimator according to the present invention. The first standby button 6 of the two-step switch 4 of the remote control handswitch 2 is pressed two times within 0.8 seconds, the collimator is turned on and off. When the execution button 8 is pressed for a second, the collimator is turned off.

Figure 7:
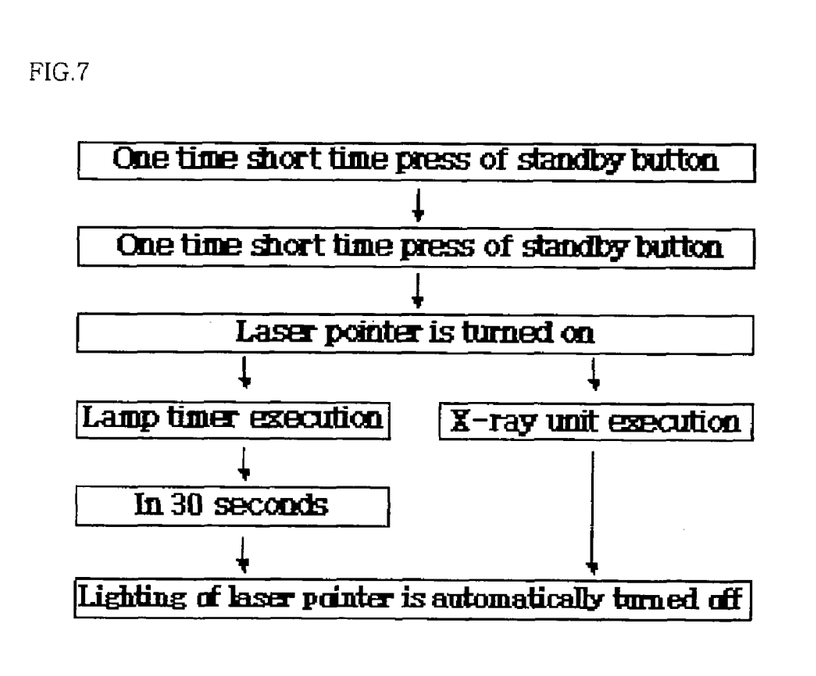
FIG. 7 is a flow chart of an on and off selection method of a laser point lighting according to the present invention.

FIG. 7 is a flow chart of an on and off selection method of the laser pointer lighting according to the present invention.

Figure 8:
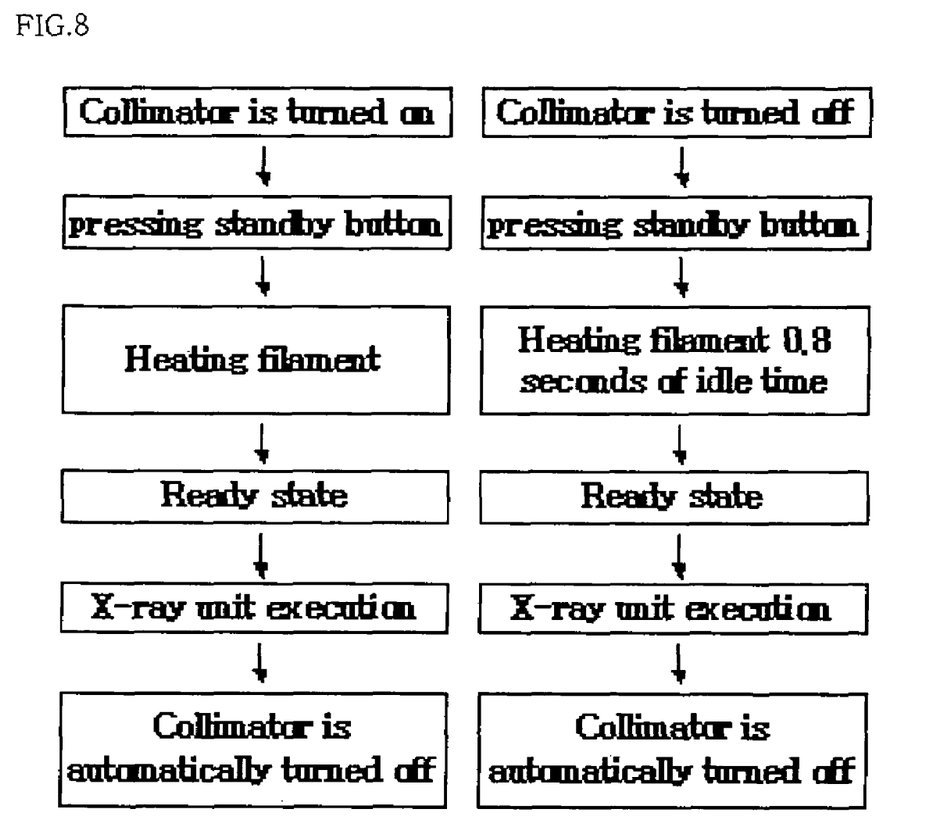
FIG. 8 is a flow chart of a filament heating and an X-ray unit execution method according to the present invention.
Figure 9:
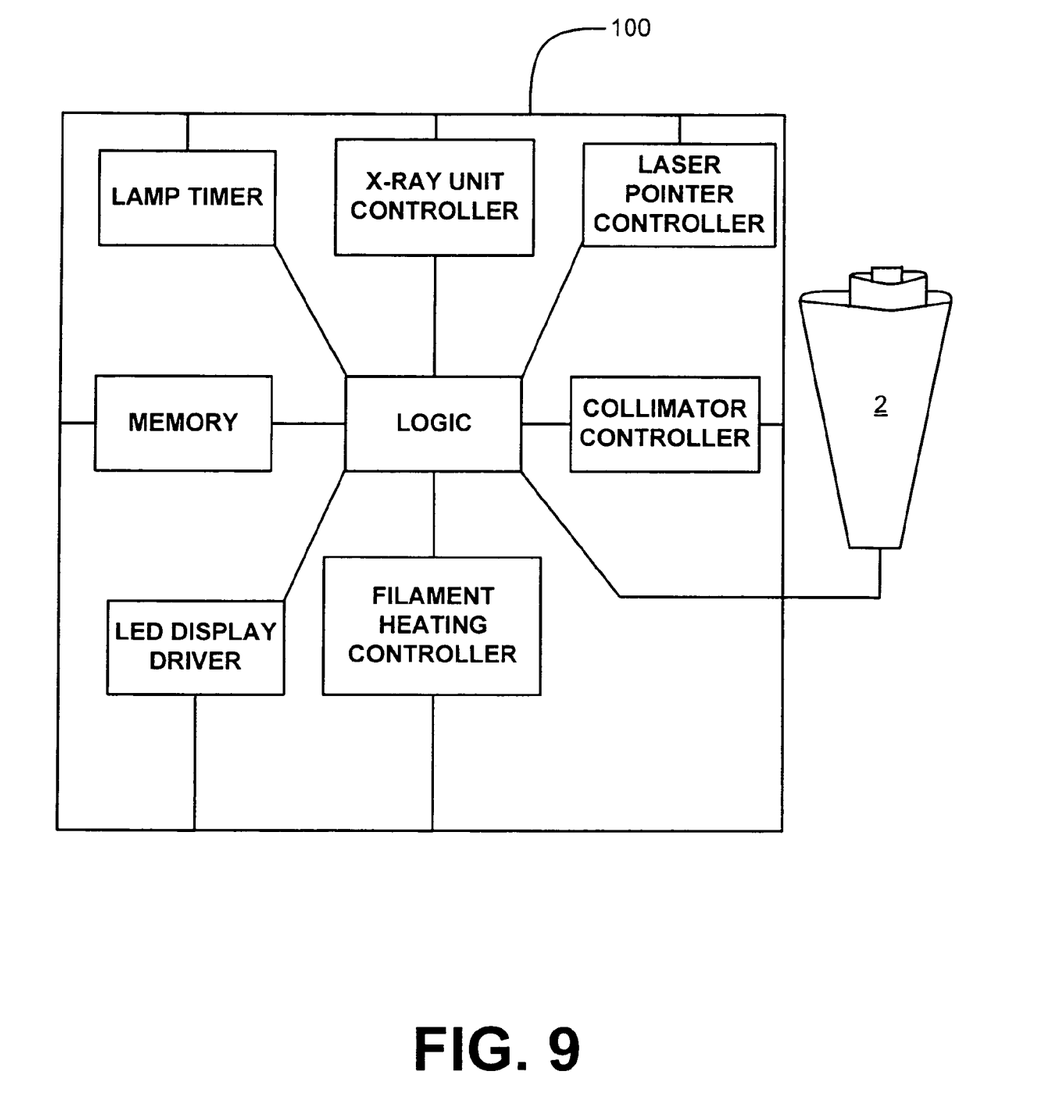
FIG. 9 is a schematic diagram of a portable X-ray unit used with a remote control handswitch for executing the operations of FIGS. 3-8 according to the present invention.

FIG. 8 is a flow chart of an execution of an X-ray when the filament is heated. As shown therein, when the collimator 6 is turned on, and the standby button 6 of the two-step switch 4 of pressed, the filament is heated. When the collimator is turned off, and the standby button 6 is pressed, the filament is heated in 0.8 seconds. After the filament is heated, the mode becomes a ready mode. The X-ray unit execution is performed.

As described above, in the present invention, it is possible to achieve a multifunction operation based on the time and number of the clicks of the standby button 6 and the execution button 8 of the two-step switch of the remote control handswitch. Namely, in the present invention, the filament heating operation, the collimator turn-on operation, the collimator turn-off operation, the APR memory selection, the storing number selection operation, and the kV and mAs selection change operations are possible based on each operation method.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. A remote control handswitch for a portable x-ray unit, comprising:
   a two-step switch formed of a standby button and an execution button; and
   a handswitch housing having the two-step switch on an upper side of the same, said handswitch housing connected to the portable x-ray unit such that
   a multi-function operation is performed with the portable x-ray unit based on a click operation of the two-step switch.

2. The handswitch of claim 1, wherein said remote control handswitch further includes a remote controller.

3. An operation method of a remote control handswitch for a portable X-ray unit, comprising:
   clicking a standby button of a two-step switch for a short period of time three times in series;
   switching the current mode to a remote control mode as a result of the clicking step;
   performing a remote control mode operation after the switching step;
   sequentially displaying a plurality of memory numbers, each memory number being associated with one of a plurality of preset memories after the performing step;
   displaying a kV value and an mAs value associated with each memory number, while the memory number is displayed in the sequentially displaying step, the displayed kV value and mAs value being blinked on the display;
   a scroll step in which the displayed memory numbers and the associated kV values and mAs values are continuously scrolled;
   clicking the standby button once, for a short period of time, when the desired memory number is displayed in the scroll step; and
   displaying the kV value and mAs value stored in the memory number selected in the clicking step.

4. An operation method of a remote control handswitch for a portable X-ray apparatus, comprising:
   clicking a standby button of a two-step switch for a short period of time three times in series;
   switching the current mode to a remote control mode as a result of the clicking step;
   performing a remote control mode operation after the switching step;
   sequentially displaying a plurality of memory numbers, each memory number being associated with one of a plurality of preset memories, after the performing step;
   displaying a kV value and an mAs value associated with each memory number, as each memory number is sequentially displayed;
   clicking a standby button once, for a short period of time, during the step in which the kV value and mAs value are displayed;
   executing a kV selection mode in response to the step in which the standby button is clicked once;
   increasing the displayed kV value by one step in response to the standby button being pressed once, after executing the kV selection mode;
   rapidly increasing or decreasing the displayed kV value, when the standby button is continuously pressed;
   in the rapidly increasing or decreasing step, selecting the displayed kV value when the standby button is released from the pressed state; and
   for both the increasing step and the rapidly increasing or decreasing step, automatically storing the displayed kV value for a certain time period after the standby button is released.

5. The method of claim 4, wherein the step in which the kV value and mAs value are displayed, further includes the steps of:
   executing an mAs selection mode in response to the step in which the standby button is clicked once;
   increasing the displayed mAs value by one step whenever the standby button is pressed once, after executing the mAs selection mode;
   rapidly increasing or decreasing the displayed mAs value when the standby button is continuously pressed for a long time;
   in the rapidly increasing or decreasing step, selecting a corresponding mAs value by releasing the standby button from the pressed state when a desired mAs value is displayed; and
   for both the increasing step and the rapidly increasing or decreasing step, automatically storing the displayed mAs value a certain time period after the standby button is released.

6. The method of claim 4, wherein a certain time period in which the kV value and mAs value are automatically stored is a time period within 5 seconds.

7. An operation method of a remote control handswitch for a portable X-ray unit, comprising the steps of:
   pressing a standby button of a two-step switch in communication with the handswitch, for a short period of time, twice within 0.8 seconds to turn on a collimator of the portable x-ray unit;
   automatically turning the collimator off using a lamp timer;
   operating the portable X-ray unit after the collimator is turned on, and prior to the collimator being automatically turned off; and
   automatically turning the collimator on and off, after the collimator is automatically turned off using the lamp timer.

8. The method of claim 7, wherein said pressing step includes the steps of:
   turning on a laser pointer;
   automatically turning off the laser pointer using a lamp timer;
   operating the portable X-ray unit while the laser pointer is on, and prior to the laser pointer being automatically turned off; and
   automatically turning the laser pointer on and off after the laser pointer is automatically turned off using the lamp timer.

9. The method of claim 7, further comprising the steps of:
   when the collimator is turned on, pressing the standby button of the two-step switch to heat a filament and perform an x-ray operation;
   while the collimator is turned off, heating the filament for a predetermined period of time when the standby button is pressed and operating the portable X-ray unit after the predetermined period of time; and
   automatically turning the collimater off after operating the portable X-ray unit.

10. The method of claim 7, wherein a short time press represents a button press for a short time period in the two-step switch, and a long time press represents a state that the button is pressed until the current mode is switched to a selection mode, wherein said short time press is performed within 0.8 seconds when pressing the standby button two times.

11. The method of claim 8, wherein a short time press represents a button press for a short time period in the two-step switch, and a long time press represents a state that the button is pressed until the current mode is switched to a selection mode, wherein said short time press is performed within 0.8 seconds when pressing the standby button two times.

12. The method of claim 9, wherein a short time press represents a button press for a short time period in the two-step switch, and a long time press represents a state that the button is pressed until the current mode is switched to a selection mode, wherein said short time press is performed within 0.8 seconds when pressing the standby button two times.

* * * * *